United States Patent [19]

Brunelle

[11] 4,138,443
[45] Feb. 6, 1979

[54] HYDRODEALKYLATION OF ALKYLAROMATIC HYDROCARBONS

[75] Inventor: Jean-Pierre Brunelle, Fresnes, France

[73] Assignee: Societe Francaise des Produits pour Catalyse "Procatalyse", Rueil Malmaison, France

[21] Appl. No.: 808,312

[22] Filed: Jun. 20, 1977

[30] Foreign Application Priority Data

Jun. 22, 1976 [FR] France .............................. 76 18961

[51] Int. Cl.$^2$ .............................................. C07C 3/58
[52] U.S. Cl. ................................................ 260/672 R
[58] Field of Search .................................... 260/672 R

[56] References Cited

U.S. PATENT DOCUMENTS

| | | | |
|---|---|---|---|
| 3,306,944 | 2/1967 | Pollitzer | 269/672 R |
| 3,560,584 | 2/1971 | Duhaut et al. | 260/672 R |
| 3,595,932 | 7/1971 | Maslyansky et al. | 260/672 R |
| 3,812,196 | 5/1974 | Uchiyama et al. | 260/672 R |
| 3,966,833 | 6/1976 | Cosyns et al. | 260/672 R |
| 3,992,468 | 11/1976 | Cosyns et al. | 260/672 R |

Primary Examiner—George Crasanakis
Assistant Examiner—C. E. Spresser
Attorney, Agent, or Firm—Bacon & Thomas

[57] ABSTRACT

A process for hydrodealkylating alkyl-substituted aromatic hydrocarbons, e.g., toluene, by reaction with hydrogen in the absence of water vapor under relatively mild reaction conditions, and a catalyst therefor are disclosed. The process is effected at a temperature of from about 450° and 650° C., preferably from about 520° to 620° C., and pressures of from about 1 to about 30, preferably from about 5 to about 20 bar, and a liquid hourly space velocity of from about 1 to about 10, preferably from about 3 to about 8, in the presence of a catalyst which comprises a metal combination of rhodium and at least one metal selected from the group consisting of copper, nickel, cobalt, iron, and zinc, and a support comprising activated alumina having a specific surface of between about 100 and about 350 m$^2$/g and a total pore volume of from about 0.5 to about 0.8 cm$^3$/g.

The activated alumina support may comprise agglomerates of active alumina obtainable by dehydrating alumina hydrate in a stream of hot gas. The agglomerates also may be previously autoclaved in an acid or neutral aqueous medium.

17 Claims, No Drawings

HYDRODEALKYLATION OF ALKYLAROMATIC HYDROCARBONS

BACKGROUND OF THE INVENTION

1. Field of the Invention

The present invention relates to a process for hydrodealkylating alkyl-substituted aromatic hydrocarbons in the presence of a multi-metal catalyst comprising a particular alumina support.

2. Description of the Prior Art

Two types of processes for hydrodealkylating alkyl-substituted aromatic hydrocarbons in a hydrogen atmosphere are presently known, that is, thermal processes and catalytic processes.

According to the first type of process, a thermal hydrodealkylation is effected in the absence of any catalyst. The need for very high reaction temperatures and pressures is an important disadvantage of such processes.

The second type of process is carried out in the presence of catalysts comprising chromium oxide, such as described in the U.S. Pat. No. 2,853,348, and usually requires lower reaction temperatures than those utilized in the thermal processes, yet same reflects the disadvantage of requiring a much too high pressure of hydrogen and the catalyst lacks stability; therefore, such processes of the second type are only of little interest in actual practice.

Among the catalytic processes employing a catalyst containing a Group VIII metal, those utilizing rhodium may be mentioned. Rhodium has long been known as being a metal which favors hydrogenolysis and hydrodealkylation. Its use in hydrodealkylation processes as an active catalyst component, in combination with a certain number of other metals, too has already been disclosed.

Thus, the U.S. Pat. No. 2,734,929 discloses the use of a catalyst comprising an alumina support and, as an active component, the combination of a metal of Group VIB and a metal of Group VIII, preferably molybdenum or cobalt.

The U.S. Pat. No. 3,306,944 discloses a hydrodealkylation catalyst comprising an alumina support and, as an active component, rhodium, ruthenium, osmium or iridium.

The U.S. Pat. Nos. 3,686,340 and 3,825,503 disclose a hydrodealkylation catalyst comprising an alumina support and, as an active component, a composition including three components comprising a noble metal of Group VIII or nickel, tin oxide or lead oxide, an alkali metal oxide or an oxide of an alkaline earth metal or a rare earth metal.

The U.S. Pat. No. 3,204,006 discloses a hydrodealkylation catalyst comprising a single noble metal of Group VIII, preferably platinum on alumina.

The U.S. Pat. No. 3,213,153 discloses a catalyst for hydrodealkylating alkyl naphthalenes which comprises, as an active component, a combination of a metal of Group VIII and a metal of Group VIA.

These prior art hydrodealkylation processes which use various catalytic formulations based on rhodium have major disadvantages. On the one hand, relatively elevated temperatures and pressures are needed for conducting same; on the other hand, they exhibit poor selectivity.

Furthermore, the stability of these catalytic formulations is usually low.

SUMMARY OF THE INVENTION

It is an object of the present invention to provide a hydrodealkylation process for alkylated aromatic hydrocarbons, which avoids these disadvantages attendant the state of the art.

It is a further object of the present invention to provide such a process which can be operated at significantly lower temperatures and pressures than those used in prior art catalytic hydrodealkylation processes.

It is a further object of the present invention to provide such a process which results in a high degree of reaction selectivity.

It is a further object to provide such a process, wherein a high degree of stability of the catalytic formulation is provided under the reaction conditions employed.

It is yet a further object of the present invention to provide a catalyst which catalyzes the hydrodealkylation of alkyl-substituted aromatic hydrocarbons at relatively mild reaction conditions, especially at relatively low temperatures and pressures.

It is still a further object of the present invention to provide such a catalyst which exhibits a high stability and which provides for a high reaction selectivity.

In order to accomplish the foregoing and other objects according to the present invention, there is provided a process for hydrodealkylating alkyl-substituted aromatic hydrocarbons, which comprises the step of reacting an alkyl-substituted aromatic hydrocarbon in the absence of water vapor with an amount of hydrogen sufficient to hydrodealkylate said alkyl-substituted aromatic hydrocarbon, in the presence of a catalyst which comprises a metal combination of rhodium and at least one metal selected from the group consisting of copper, nickel, cobalt, iron and zinc, and a support comprising activated alumina having a specific surface of between about 100 and about 350 m$^2$/g and a total pore volume of from about 0.5 to about 0.8 cm$^3$/g, at a reaction temperature and pressure and a liquid hourly space velocity sufficient to effect a hydrodealkylation of the alkyl-substituted aromatic hydrocarbon.

Preferably, the molar ratio between the alkyl-substituted aromatic hydrocarbon and the hydrogen is between about 1:10 and about 1:1. The reaction is preferably carried out at a temperature of between about 450° and about 650° C and a pressure of between about 1 and about 30 bars.

The liquid hourly space velocity preferably is a space velocity of between about 1 to about 10 volumes of the liquid per volume of the catalyst, per hour.

The activated alumina of the catalyst support preferably comprises agglomerates of active alumina obtained by dehydrating alumina hydrate in a stream of hot gas.

The above-described agglomerates of active alumina may have been previously autoclaved in an acid or neutral aqueous medium.

According to a preferred embodiment of the invention, the catalyst may further include a metal selected from the group consisting of platinum and palladium.

According to the present invention, there is further provided a catalyst for catalyzing the above hydrodealkylation, which comprises a metal combination of rhodium and at least one metal selected from the group consisting of copper, nickel, cobalt, iron, and zinc, and a support comprising activated alumina having a specific surface of between about 100 and about 350 m$^2$/g and a total pore volume of from about 0.5 to about 0.8 cm$^3$/g.

Further objects, features and advantages of the present invention will become apparent from the following detailed description of the invention and its preferred embodiments.

DETAILED DESCRIPTION OF THE INVENTION

It has now been found that the above catalysts containing a combination of several metals, including rhodium, and the particular alumina support according to the present invention, catalyze the hydrodealkylation of alkyl-substituted aromatic hydrocarbons in a hydrogen atmosphere, in the absence of water vapor, under certain reaction conditions, namely, those of temperature and pressure, which are markedly milder than those used in the thermal or catalytic prior art processes, and provides for a very high degree of stability of the catalyst under these reaction conditions and a high degree of selectivity of the reaction.

One advantage of the present invention resides in the fact that the presence of rhodium and, optionally, platinum and/or palladium, and at least one other metal selected from the group consisting of copper, nickel, cobalt, iron and zinc deposited onto the particular alumina support results in catalysts which are significantly more active, selective and stable vis-a-vis those disclosed in the prior art.

Another practical advantage of the present invention resides in the fact that the optional replacement of part of the rhodium by platinum and/or palladium permits the significant reduction in catalyst production costs and, at the same time, permits also improvement in catalytic properties.

The support for the catalyst according to the present invention may comprise active alumina which is obtained according to the process disclosed in the U.S. Pat. No. 2,915,365, the disclosure of which is hereby incorporated by reference and relied upon, and which alumina has been agglomerated according to the process disclosed in the U.S. Pat. No. 2,881,051, the disclosure of which is also hereby incorporated by reference and relied upon.

The process disclosed in the U.S. Pat. No. 2,915,365 comprises the transforming of hydrated alumina into an active alumina having a high absorption capacity, and includes the following steps:

[a] contacting the finely divided hydrated alumina with a stream of hot gas at a temperature between 400° and 1,000° C;

[b] maintaining the contact between the hydrated alumina and the gas for a period of time of between a fraction of a second and 10 seconds; and,

[c] separating the partially dehydrated alumina from the hot gases.

This active alumina which is used according to the process of the present invention must exhibit a specific surface of between about 150 and about 350 m$^2$/g and a total pore volume of between about 0.5 and about 0.8 cm$^3$/g. Its sodium hydroxide content preferably is between about 0.05 and about 1% by weight relative to the alumina. The surface acidity of such catalyst which is determined by the degree of conversion of butene-1 into isobutene at 500° C, preferably is about 2 to about 6 times weaker than that of alumina supports having a cubic gamma and/or eta structure which are conventionally used in catalytic reforming processes. This acidity is determined according to conventional test methods for isomerizing butene-1 into isobutene. This method comprises desorbing a 1 g sample of the respective support at 500° C under a stream of helium, then injecting thereinto a charge of 3 ml of butene-1 at the same temperature of 500° C under atmospheric pressure. The determination of reaction products is effected at the outlet of the reactor by gas chromatography.

According to another embodiment of the present invention the catalyst support can be obtained by autoclaving the abovedescribed agglomerates of active alumina in an aqueous medium, optionally in the presence of an acid, at a temperature of above 100° C, preferably of between about 150 and about 250° C, during a period of time of preferably between about 1 and about 20 hours and subsequently drying and calcining same. The calcination temperature is adjusted in such a way that a specific surface of preferably between about 100 and about 170 m$^2$/g and a pore volume of preferably between about 0.5 and about 0.8 cm$^3$/g are obtained. The resulting alumina has a gamma tetragonal crystallographical structure. The preparation of such a support is disclosed in the French Pat. Nos. 1,449,904 and 1,386,364, the disclosure of which is hereby incorporated by reference.

The catalyst according to the present invention comprises rhodium, at least one other metal selected from the group consisting of nickel, copper, cobalt, iron, and zinc, and, optionally, yet another metal selected from the group consisting of platinum and palladium.

The rhodium, the platinum, and the palladium are deposited on the support in amounts of from about 0.05 to about 5%, preferably from about 0.1 to about 1%, by weight, relative to the support, whereby the per weight ratio between the amount of rhodium and the amount of the other two noble metals of Group VIII, which optionally are present, may vary within large limits, but preferably is between about 1:5 and about 5:1.

The content of the other metals, nickel, copper, cobalt, iron, and zinc, may vary between about 0.10 and about 20%, preferably between about 0.50 and about 5% by weight relative to the support.

The catalyst can be prepared according to usual methods which comprise impregnating the support or carrier with solutions of inorganic or organic compounds of the metals which are intended to be deposited. The impregnation may be carried out with a solution containing all of the metals, or with different solutions successively. As examples of soluble compounds of rhodium, platinum, palladium, and the non-noble metals above mentioned, the following are exemplary: rhodium trichloride, chloroplatinic acid, palladium-II chloride, nitrates of cobalt, nickel, iron, copper and zinc, and the like. A homogeneous impregnation can be advantageously achieved by adding about 0.1 to about 10% of an inorganic or organic acid to the solution of the metal compounds. Usually, nitric acid or acetic acid is utilized.

After impregnating the support with any above solution, the catalyst is subsequently dried and then calcined in a stream of air at about 300° to about 800° C, for several hours.

Finally the catalyst is reduced under a hydrogen atmosphere at a temperature of between about 300° to 650° C, for about 1 to 10 hours. The reduction of the catalyst can advantageously be carried out in the hydrodealkylation reactor. Reducing agents other than hydrogen too can be used.

The catalyst may advantageously be treated in an atmosphere containing a sulfur compound such as hydrogen sulfide. The sulfurizing step can be effected at any stage during the preparation of the catalyst, after the impregnation of the support but preferably before calcination.

The catalyst may be prepared in the form of spheres, extruded particles, pellets, or any other shape.

The hydrodealkylating reaction is effected in at least one reactor, whether drawing from fixed bed, mobile bed or fluidized bed techniques, and, optionally, providing for the alternative of regenerating the catalyst in a continuous or batch operation.

The reaction is effected at a temperature of between about 450° and about 650° C, preferably between about 520° and about 620° C; the pressure is between about 1 and 30 bar, preferably between about 5 and about 20 bar.

The hourly space velocity is between about 1 and about 10, preferably between 3 and 8 volumes of liquid, per volume of catalyst, per hour.

The process according to the present invention is generally used for hydrodealkylating alkyl-substituted aromatic hydrocarbons. As alkyl-substituted aromatic hydrocarbons for which the process is especially suited, there may be mentioned benzene or naphthene which are substituted by at least one lower alkyl group having from 1 to 5 carbon atoms, preferably a methyl group, for example, lower alkyl-substituted benzenes, such as, toluene and the xylenes.

The hydrodealkylating reaction may be effected upon a starting material containing either an above-mentioned aromatic hydrocarbon, in pure form, or upon a mixture of these hydrocarbons, optionally in the presence of other hydrocarbons such as paraffins.

Without limiting the present invention, the following examples are intended to further illustrate [1] the use of the multi-metal combinations according to the present invention deposited on the particular supports described above, and, [2] their specific advantages as compared with catalyst wherein rhodium is deposited on a different alumina support.

EXAMPLE 1

In this example, several trimetal catalysts which are representative of the catalyst according to the present invention are described.

100 g of small alumina spheres having a gamma tetragonal structure, prepared according to the French Pat. No. 1,449,904 by autoclaving agglomerates of active alumina in the presence of acetic acid and subsequent drying and calcination, and which exhibited a specific surface of 120 $m^2/g$, a pore volume of 0.6 $cm^3/g$ and a sodium hydroxide content of 1,000 ppm, were impregnated with 60 ml of an aqueous solution containing 1.5 g of nitric acid, 0.15 g of rhodium in the form of rhodium trichloride, 0.10 g of palladium in the form of palladium II chloride and 0.5 g of a non-noble metal selected from the group of copper, nickel, cobalt, iron and zinc in the form of a nitrate.

After several hours of impregnation, the spheres were dried at 120° C and then calcined at 600° C under air, for 3 hours.

The catalysts (A), (B), (C), (D), and (E) which were obtained according to this method contained 0.15% by weight of rhodium, 0.10% by weight of palladium, and 0.5% by weight of copper, nickel, cobalt, iron and zinc, respectively.

EXAMPLE 2

The procedure of Example 1 was repeated, using an impregnating solution containing 0.15 g of rhodium in the form of rhodium trichloride, 0.20 g of platinum in the form of chloroplatinic acid and 0.50 g of copper in the form of copper nitrate.

The catalyst (F) which was obtained after drying and calcination contained 0.15% by weight of rhodium, 0.20% by weight of platinum and 0.50% by weight of copper.

EXAMPLE 3

100 g of small active alumina spheres which were obtained according to the process disclosed in the U.S. Pat. No. 2,915,365, and which exhibited a specific surface of 250 $m^2/g$, a pore volume of 0.60 $cm^3/g$, a sodium hydroxide content of 1,000 ppm, and a surface acidity corresponding to conversion of butene-1 into isobutene at 500° C of 12.5%, were impregnated with 60 ml of an aqueous solution of sodium trichloride, palladium-II-chloride and copper nitrate, containing 0.15 g of rhodium, 0.10 g of palladium, 0.50 g of copper and 0.340 g of nitric acid.

The catalyst (G) which was obtained after drying and calcination at 600° C, contained 0.15% by weight of rhodium, 0.10% by weight of palladium and 0.50% by weight of copper.

The catalysts (F) and (G) also illustrate the present invention.

Hereinafter, for purposes of clarity, the catalysts according to the present invention which are described in Examples 1 and 3 will be designated "flash alumina" and "autoclaved flash alumina," respectively.

EXAMPLE 4

In this comparative example, the preparation of a catalyst is described containing only rhodium as an active component, but nevertheless utilizing a support according to the invention.

The preparation was identical to that described in the preceding examples, with the only difference being employment of a rhodium trichloride solution containing 0.15 g of rhodium.

The catalysts (H) and (I) which were obtained according to this procedure contained 0.15% by weight of rhodium deposited on a flash alumina having a specific surface of 250 $m^2/g$, such as described in Example 3, or on an autoclaved flash alumina having a specific surface of 120 $m^2/g$, such as described in Example 1, respectively.

In order to demonstrate the advantage attendant the use of a multi-metal formulation according to the present invention, as compared with prior art mono-metal catalysts, the results obtained in catalytic tests with the above catalysts can be compared with those obtained with catalysts according to the present invention, namely, in the case of the catalyst (H), with those from the catalyst (G), and in the case of the catalyst (I), with those obtained from the catalysts (A), (B), (C), (D), (E) and (F).

EXAMPLE 5

100 g autoclaved flash alumina such as described in Example 1 were impregnated with an aqueous solution of rhodium trichloride and a nitrate of copper, nickel, and iron, respectively, containing 0.50 g of rhodium, 1.0 g of copper, nickel, or iron, and 1.5 g of nitric acid.

After several hours of contact, the spheres were dried at 120° C and then dried, calcined at 600° C under air for 3 hours.

The catalysts (J), (K), (L) which were obtained according to this procedure, contained 0.5% by weight of rhodium and 1.0% of copper, nickel, and iron, respectively. They are examples of catalysts according to the present invention, wherein the formulation is richer in rhodium than the preceding formulation and no noble metal of Group VIIIC of the Periodic Table is present.

EXAMPLE 6

The method of Example 5 was repeated utilizing an impregnating solution containing 0.50 g of rhodium in the form of rhodium trichloride, 0.5 g of nickel in the form of nickel nitrate, 0.5 g of iron in the form of iron-III-nitrate and 1.5 g of nitric acid.

The resulting catalyst (M) contained 0.5% by weight of rhodium, 0.5% by weight of nickel, and 0.5% by weight of iron.

EXAMPLE 7

The catalyst (N) described in this example is a comparative catalyst for comparison with the catalysts (J), (K), (L), and (M) according to the present invention. It contained 0.5% by weight of rhodium deposited on a support of autoclaved flash alumina and was prepared according to the method described in the examples hereinabove.

EXAMPLE 8

The catalysts (O) and (P) which are described below also were prepared for comparative purposes for evaluating the catalytic activity of rhodium in combination with copper, deposited on supports other than those according to the present invention. Their behavior can be compared with that of catalyst (J) according to the present invention.

The catalysts (O) and (P) contained 0.5% by weight of rhodium and 1% by weight of copper deposited on a support of α-alumina exhibiting a specific surface of 10 $m^2/g$ and a pore volume of 0.60 $cm^3/g$ or on a support of an alumina of gamma cubic structure exhibiting a specific surface of 200 $m^2/g$ and a pore volume of 0.55 $cm^3/g$, respectively. The latter alumina which is conventionally used for catalytic reforming actions exhibits a surface acidity corresponding to a conversion of butene-1 to isobutene at 500° C of 40%.

EXAMPLE 9

In this example, the preparation of two catalysts is described which contain platinum or palladium deposited on a flash alumina such as described in Example 3, which corresponds to the present invention.

100 g of small flash alumina spheres exhibiting a specific surface of 250 $m^2/g$ and a pore volume of 0.60 $cm^3/g$, were impregnated with 60 ml of an aqueous solution of chloroplatinic acid or of palladium II chloride containing 0.50 g of the noble metal and 3.4 g of nitric acid in both cases. After several hours of impregnation, the spheres were dried at 120° C and then calcined at 600° C under air for 3 hours.

The resulting catalysts (Q) and (R) contained 0.5% by weight of platinum or 0.5% by weight of palladium, respectively.

EXAMPLE 10

The catalyst (S) which is described in this example represents a conventional prior art catalytical formulation which gives good results at more elevated reaction temperatures and pressures. This catalyst contained 10% by weight of chromium oxide, $Cr_2O_3$, and was prepared by impregnating an alumina having a gamma cubic structure, such as described in Example 8, with a solution of chromic acid.

After 3 hours of calcination at 600° C, the catalysts (A), (B), (C), (D), (E), (F), (G), (H), (I), (J), (K), (L), (M), (N), (O), (P), (Q), (R), and (S) prepared according to the Examples 1–10, all were reduced under a hydrogen blanket at 550° C for 2 hours, and then were tested in the absence of water vapor in a pilot plant assembly for hydrodealkylating toluene into benzene under the following reaction conditions:

Pressure: 10 bar
Temperature: 570° C
Molar ratio hydrogen/toluene: 5
Liquid space velocity: 4 volumes of liquid per volume of catalyst per hour.

The conversions, selectivities and yields which were obtained after 3, 24 and 76 hours of continuous reaction, as well as the percentages of carbon which were deposited on the catalysts after 76 hours of reaction, are given in Table I. From these data, the superior performance of the catalysts (A), (B), (C), (D), (E), (F), (G), (J), (K), (L) and (M) according to the present invention is apparent: on the one hand, as compared with that of catalysts (H), (J), and (N) containing only rhodium deposited on a support according to the present invention; and, on the other hand, as compared with the catalysts (O) and (P) containing metal combinations according to the present invention but which are deposited on supports other than those described as within the ambit of the present invention.

Furthermore, the two noble metals of the Group VIIIC, namely, platinum and palladium (see catalysts Q and R) and the prior art catalyst (S) containing chromium, exhibit markedly lower hydrodealkylating activity under these test conditions.

EXAMPLE 11

In order to reflect the disadvantageous influence of the presence of water vapor during the hydrodealkylating reaction, catalyst (A) was also tested under the same reaction conditions as described above, but utilizing toluene which had not been dried and which contained but 300 ppm of water. After several hours of reaction, a marked decrease in conversion resulted.

TABLE I

| Example No. | Reaction period in hours (3 24 76) | Conversion 3 | | 24 | 76 | Selectivity 3 | 24 | 76 | Yield 3 | 24 | 76 | % per weight of carbon 76 |
|---|---|---|---|---|---|---|---|---|---|---|---|---|
| 1 | Catalyst A 0.15% Rh + 0.10% Pd + 0.5% Cu Autoclaved flash alumina | 83 | | 69 | 62 | 87 | 98 | 99 | 73 | 67 | 61 | 1.55 |
| 1 | Catalyst B 0.15% Rh + 0.10% Pd + 0.5% Ni | 88 | | 63 | 59 | 76 | 98 | 99 | 67 | 62 | 59 | 1.85 |

TABLE I-continued

| Example No. | Reaction period in hours (3 24 76) | Conversion 3 | Conversion 24 | Conversion 76 | Selectivity 3 | Selectivity 24 | Selectivity 76 | Yield 3 | Yield 24 | Yield 76 | % per weight of carbon 76 |
|---|---|---|---|---|---|---|---|---|---|---|---|
| 1 | Autoclaved flash alumina Catalyst C 0.15% Rh + 0.10% Pd + 0.5% Co | 86 | 73 | 66 | 76 | 99 | 99 | 65 | 72 | 66 | 1.30 |
| 1 | Autoclaved flash alumina Catalyst D 0.15% Rh + 0.10% Pd + 0.5% Zn | 62 | 60 | 56 | 98 | 97 | 99 | 61 | 62 | 56 | 1.30 |
| 1 | Autoclaved flash alumina Catalyst E 0.15% Rh + 0.10% Pd + 0.5% Fe | 73 | 68 | 59 | 79 | 95 | 99 | 58 | 65 | 59 | 1.90 |
| 2 | Autoclaved flash alumina Catalyst F 0.15% Rh + 0.20% Pt + 0.5% Cu | 84 | 82 | 58 | 90 | 96 | 98 | 76 | 79 | 57 | 1.0 |
| 3 | Autoclaved flash alumina Catalyst G 0.15% Rh + 0.10% Pd + 0.5% Cu | 48 | 64 | 60 | 96 | 97 | 98 | 46 | 62 | 59 | 1.25 |
| Comparative 4 | Flash alumina Catalyst H 0.15% Rh | 4 | 10 | 15 | 98 | 98 | 98 | 4 | 10 | 15 | 1.10 |
| Comparative 4 | Flash alumina Catalyst I 0.15% Rh | 65 | 38 | 30 | 94 | 95 | 98 | 61 | 38 | 29 | 1.30 |
| 5 | Autoclaved flash alumina Catalyst J 0.5% Rh + 1% Cu | 83 | 77 | 80 | 55 | 89 | 97 | 46 | 68 | 78 | 2.60 |
| 5 | Autoclaved flash alumina Catalyst K 0.5% Rh + 1% Ni | 89 | 83 | 82 | 52 | 91 | 95 | 46 | 75 | 78 | 3.10 |
| 5 | Autoclaved flash alumina Catalyst L 0.5% Rh + 1% Fe | 81 | 76 | 72 | 59 | 93 | 97 | 48 | 71 | 70 | 2.30 |
| 6 | Autoclaved flash alumina Catalyst M 0.5% Rh + 0.5% Ni + 0.5% Fe | 84 | 81 | 80 | 54 | 89 | 95 | 45 | 72 | 76 | 2.90 |
| Comparative 7 | Autoclaved flash alumina Catalyst N 0.5% Rh | 78 | 74 | 45 | 59 | 84 | 92 | 38 | 62 | 41 | 6.40 |
| Comparative 8 | Autoclaved flash alumina Catalyst O 0.5% Rh + 1% Cu | 52 | 43 | 12 | 49 | 53 | 96 | 25 | 23 | 11 | 1.50 |
| Comparative 8 | α-alumina Catalyst P 0.5% Rh + 1% Cu | 63 | 73 | 55 | 37 | 45 | 44 | 23 | 33 | 24 | 9.2 |
| Comparative 9 | γc-alumina Catalyst Q 0.5% Pt | 4 | 5 | 5 | 97 | 98 | 97 | 4 | 5 | 5 | 1.60 |
| Comparative 9 | Flash alumina Catalyst R 0.5% Pd | 0.5 | 0.7 | 0.7 | 98 | 99 | 99 | 0.5 | 0.7 | 0.7 | — |
| Comparative 10 | Flash alumina Catalyst S 10% $Cr_2O_3$ | 4 | 2 | 0.5 | 99 | 100 | 100 | 4 | 2 | 0.5 | — |
| 11 | γc-alumina Catalyst A 0.15% Rh + 0.10% Pd + 0.5% Cu Autoclaved flash alumina 300 ppm of water in the reaction mixture | 84 | 63 | 45 | 99 | 99 | 99 | 74 | 63 | 45 | 1.40 |

While the invention has now been described in terms of various preferred embodiments, the skilled artisan will readily appreciate that various substitutions, modifications, changes, and omissions, may be made without departing from the spirit thereof. Accordingly, it is intended that the scope of the present invention be limited solely by that of the following claims.

What is claimed is:

1. A process for hydrodealkylating alkyl-substituted aromatic hydrocarbons, which comprises the step of reacting an alkyl-substituted aromatic hydrocarbon, in the absence of water vapor with an amount of hydrogen which is equivalent to a molar ratio between the alkyl-substituted aromatic hydrocarbon and the hydrogen of between about 1:10 to about 1:1, at a temperature of between about 450° and about 650° C, and under a pressure of about 1 to about +bars and a space velocity of between about 1 to about 10 volumes of the liquid per volume of the catalyst, per hour, in the presence of a catalyst which comprises a metal combination of rhodium and at least one metal selected from the group consisting of copper, nickel, cobalt, iron, and zinc, and a support comprising activated alumina selected from the group consisting of agglomerates of active alumina obtained by dehydrating alumina hydrate in a stream of hot gas and agglomerates of active alumina having a gamma tetragonal crystallographical structure obtained by autoclaving agglomerates of active alumina in an acid or neutral aqueous medium said activated alumina having a specific surface of between about 100 and about 350 m$^2$/g and a total pore volume of from about 0.5 to about 0.8 cm$^3$/g.

2. The process as defined in claim 1, wherein the catalyst support comprises agglomerates of active alumina obtained by dehydrating alumina hydrate in a stream of hot gas.

3. The process as defined in claim 1, wherein the catalyst support comprises agglomerates of active alumina having a gamma tetragonal crystallographical structure obtained by autoclaving agglomerates of active alumina in an acid or neutral aqueous medium.

4. The process as defined in claim 1, wherein the combination of metals in the catalyst further comprises at least one metal selected from the group consisting of platinum and palladium.

5. The process as defined in claim 1, wherein the combination of metals in the catalyst comprises rhodium and copper.

6. The process as defined in claim 1, wherein the combination of metals in the catalyst comprises rhodium and nickel.

7. The process as defined in claim 1, wherein the combination of metals in the catalyst comprises rhodium and cobalt.

8. The process as defined in claim 1, wherein the combination of metals in the catalyst comprises rhodium and iron.

9. The process as defined in claim 1, wherein the combination of metals in the catalyst comprises rhodium and zinc.

10. The process as defined in claim 4, wherein the combination of metals in the catalyst comprises palladium.

11. The process as defined in claim 4, wherein the combination of metals in the catalyst comprises platinum.

12. The process as defined in claim 1, wherein the pressure is between about 5 and about 20 bars and the temperature is between about 520° and about 620° C.

13. The process as defined in claim 1, wherein the liquid space velocity is between about 3 and about 8 volumes of liquid per volume of catalyst per hour.

14. The process as defined in claim 1, wherein the molar ratio between the hydrogen and the hydrocarbon is between about 3 and about 8.

15. The process as defined in claim 1, wherein the specific surface of the catalyst support is between about 150 and about 350 m$^2$/g.

16. The process as defined in claim 1, wherein the specific surface of the catalyst support is between about 100 and about 170 m$^2$/g.

17. The process as defined in claim 1, wherein the alkyl-substituted aromatic hydrocarbon is a monocyclic aromatic hydrocarbon.

* * * * *